United States Patent [19]

Flaugh

[11] Patent Number: 4,576,959

[45] Date of Patent: Mar. 18, 1986

[54] 6-SUBSTITUTED-4-DIALKYLAMINOTETRAHYDROBENZ[C,D]INDOLES

[75] Inventor: Michael E. Flaugh, Indianapolis, Ind.

[73] Assignee: Eli Lilly and Company, Indianapolis, Ind.

[21] Appl. No.: 697,292

[22] Filed: Feb. 1, 1985

Related U.S. Application Data

[63] Continuation-in-part of Ser. No. 577,096, Feb. 6, 1984.

[51] Int. Cl.[4] .................... A61K 31/40; C07D 209/90
[52] U.S. Cl. ........................ 514/411; 548/436
[58] Field of Search ............... 548/436; 424/274; 514/411

[56] References Cited

U.S. PATENT DOCUMENTS

| | | | |
|---|---|---|---|
| 3,200,130 | 8/1965 | Szmuszkovicz | 548/436 |
| 3,336,307 | 8/1967 | Shen | 548/436 |
| 4,110,339 | 8/1978 | Bach et al. | 260/326.9 |
| 4,282,240 | 8/1981 | Baldwin | 548/436 |

OTHER PUBLICATIONS

Harris et al., *J.P.E.T.*, 128 358 (1960).
Kruse et al., J. Org. Chem., 49, 4761 (1984), (12/15/84 issue).
Haefliger et al., *Tetrahedron Letters*, 25, 285 (1983).
Haefliger et al., ibid, 289.
Haefliger, *H.C.A.*, 67, 1942 (1984).

*Primary Examiner*—Donald G. Daus
*Assistant Examiner*—Robert Benson
*Attorney, Agent, or Firm*—James L. Rowe; Arthur R. Whale

[57] ABSTRACT

(±)-4-substitutedamino-6-substituted-1,3,4,5-tetrahydrobenz[c,d]indoles and pharmaceutically acceptable salts thereof, useful as anti depressants.

23 Claims, No Drawings

6-SUBSTITUTED-4-DIALKYLAMINOTETRAHYDROBENZ[C,D]INDOLES

CROSS-REFERENCE

This application is a continuation-in-part of my copending application Ser. No. 577,096 filed 2-6-84.

BACKGROUND OF THE INVENTION

The benz[c,d]indole ring system (I) has been known since 1949.

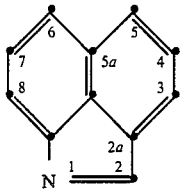

For example Uhle et al. *J. Am. Chem. Soc.*, 71, 1611 (1949); ibid, 73, 2402 (1951); Grob et al. *Helv. Chim. Acta.*, 33, 1796, 1955 (1950), 35, 2095 (1952), 36, 839 (1953) and Stoll et al. ibid, 33, 2254, 2257 (1950); 35, 148 (1952), prepared, among other compounds, a 5-keto-1,3,4,5-tetrahydrobenz[c,d]indole plus the corresponding 4-amino and 4-acetylamino derivatives. A useful starting material for the synthesis of these compounds was a 1-benzoyl-1,2,2a,3,4,5-hexahydro derivative, II.

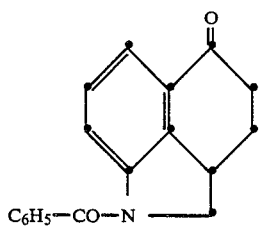

formed by the Friedel-Crafts ring closure of 1-benzoyl-2(3-indolinyl)propionylchloride. Kornfeld et al., *J.A.C.S.*, 78, 3087 (1956) also prepared this compound and converted it, via a series of intermediates, to the 4-amino-5-keto derivative which was, in itself, a key intermediate in the first total synthesis of lysergic acid. In this synthetic procedure, a fourth ring (an N-methyl piperidine ring) was grafted onto an appropriately substituted tricyclic 1,2,2a,3,4,5-hexahydrobenz[c,d]indole. Stoll et al. *Helv. Chim. Acta*, 35, 148 (1952) also prepared (±)-4-dimethylamino-1,3,4,5-tetrahydrobenz[c,d]indole. Bach and Kornfeld, U.S. Pat. No. 4,110,339, prepared the corresponding 4-(di-n-propyl)amino compound. Ledelec et al, U.S. Pat. No. 4,447,438 discloses 4-piperidyl-substituted-1H-indole having dopaminergic properties.

Certain naturally occurring alkaloids, agroclavine and elymoclavine, have been converted by Cassady et al. *J. Med. Chem.*, 17, 300 (1974) to N-methyldioxychanoclavine, N-methylchanoclavine, and chanoclavine, all 4,5-disubstituted tetrahydrobenz[c,d]indoles (III).

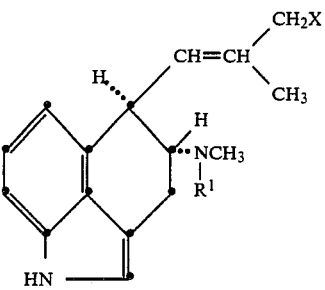

wherein X is H or OH and $R^1$ is $CH_3$ or H. Compounds according to III were without significant prolactin inhibiting activity, unlike the Bach-Kornfeld (±)-4-(di-n-propyl)amino-1,3,4,5-tetrahydrobenz[c,d]indole, which was found to be a selective dopamine agonist as shown by its action in inhibiting dopamine uptake in bovine striatal membrane in vitro. The corresponding 4-(dimethyl)amino derivative of Stoll et al. (loc. cit.) was used only as an intermediate. The 4-aminotetrahydrobenz[c,d]indoles and related derivatives are weak serotonin antagonists with one exception, the 4-acetylamino-5-oxo derivative—see Harris and Uhle, *J. Pharm. & Exper. Therap.*, 128, 358 (1960).

SUMMARY OF THE INVENTION

This invention provides 4-aminosubstituted-6-substituted-1,3,4,5-tetrahydrobenz[c,d]indoles of the formula

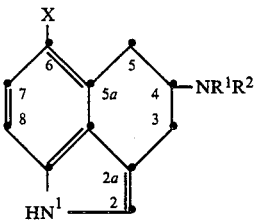

wherein $R^1$ and $R^2$ are individually hydrogen, methyl, ethyl, n-propyl or allyl; $R^1$ can be additionally Y—CO where Y is H, methyl ethyl or vinyl; and X is a halogen (such as Cl, Br, I or F), CN, $CONH_2$, $NH_2$ or $NO_2$, and pharmaceutically acceptable acid addition salts thereof.

Compounds according to IV in which X is $NO_2$, Br or CN are, in addition, useful intermediates for preparing other compounds coming within the scope of this invention. Illustrative of those groups which $NR^1R^2$ represents are included amino, methylamino, n-propylamino, ethyl-n-propylamino, diethylamino, ethylamino, n-propylamino and the like groups.

Pharmaceutically-acceptable acid addition salts of the compounds of formula IV include salts derived from non-toxic inorganic acids such as: hydrochloric acid, nitric acid, phosphoric acid, sulfuric acid, hydrobromic acid, hydriodic acid, phosphorous acid and others, as well as salts derived from non-toxic organic acids such as aliphatic mono and dicarboxylic acids, phenyl-substituted alkanoic acids, hydroxyalkanoic and hydroxyalkandioic acid, aromatic acids, aliphatic and aromatic sulfonic acids. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hyroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, naphthalene-1-sulfonate, naphthalene-2-sulfonate and mesylate.

The compounds of formula IV are central serotonin agonists, useful as anti-depressants. Thus, included within the present invention is a pharmaceutical formulation which comprises as an active ingredient a compound of formula IV, or a pharmaceutically-acceptable acid addition salt thereof, associated with one or more pharmaceutically-acceptable carriers or excipients therefor. The formulation or the active ingredient thereof can be used as a method of treating depression, obesity, alcoholism, smoking, or senile dementia in a warm-blooded animal by administering to said animal a therapeutically-effective amount of a compound of formula IV, or a pharmaceutically-acceptable acid addition salt thereof.

Compounds according to formula IV have an asymmetric center at C-4 and thus occur as a (±) or dl, racemic mixture. This invention includes both the racemates and the individual stereoisomers represented by formula IV. The individual stereoisomers can be prepared by resolving a racemate of a 2,2a-dihydro indole intermediate (XIV, XIVa, XV, XVa, XVI, XVIa from Reaction Scheme 2 below or XXX from Reaction 1), then oxidizing the separated stereoisomer to the indole and carrying out any further reactions to obtain a desired optically-active product of formula IV. The resolution procedure can employ optically-active acids such as, for example, L-(+)-R-tartaric acid, (−)-dibenzoyltartaric acid, (+)-camphoric acid, (+)-10-camphorsulfonic acid, (+)-mandelic acid, (−)-malic acid, N-acetyl-L-glutamic acid, t-BOC-D-phenyl glycine, D-(−)-S-tartaric acid, L-p-toluoyltartaric acid and the like.

Compounds illustrative of the scope of this invention include:

(±)-4-diallylamino-6-chloro-1,3,4,5-tetrahydrobenz[c,d]indole sulfate (±)-4-methylethylamino-6-bromo-1,3,4,5-tetrahydrobenz[c,d]indole tartrate (+)-4-dimethylamino-6-iodo-1,3,4,5-tetrahydrobenz[c,d]indole maleate (±)-4-diallylamino-6-amino-1,3,4,5-tetrahydrobenz[c,d]indole succinate (±)-4-diethylamino-6-nitro-1,3,4,5-tetrahydrobenz[c,d]indole phosphate (−)-4-methyl-n-propylamino-6-aminocarbonyl-1,3,4,5-tetrahydrobenz[c,d]indole dihydrogenphosphate (±)-4-(di-n-propyl)amino-6-aminocarbonyl-1,3,4,5-tetrahydrobenz[c,d]indole bisulfate (±)-4-dimethylamino-6-aminocarbonyl-1,3,4,5-tetrahydrobenz[c,d]indole hydrobromide (±)-4-diethylamino-6-aminocarbonyl-1,3,4,5-tetrahydrobenz[c,d]indole tosylate (−)-4-diallylamino-6-aminocarbonyl-1,3,4,5-tetrahydrobenz[c,d]indole malate (±)-4-(di-n-propyl)amino-6-bromo-1,3,4,5-tetrahydrobenz[c,d]indole benzoate (−)-4-diethylamino-6-fluoro-1,3,4,5-tetrahydrobenz[c,d]indole phenylacetate (+)-4-dimethylamino-6-chloro-1,3,4,5-tetrahydrobenz[c,d]indole 1,4-butyndioate (±)-4-diallylamino-6-nitro-1,3,4,5-tetrahydrobenz[c,d]indole hydrochloride (±)-4-dimethylamino-6-amino-1,3,4,5-tetrahydrobenz[c,d]indole sulfate (+)-4-(di-n-propyl)amino-6-cyano-1,3,4,5-tetrahydrobenz[c,d]indole fumarate (−)-4-amino-6-bromo-1,3,4,5-tetrahydrobenz[c,d]indole propiolate and the like.

Compounds according to IV above wherein X is F can be prepared according to the following reaction scheme.

Reaction Scheme 1

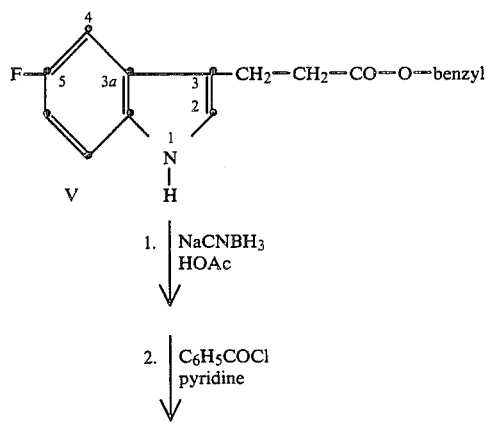

-continued
Reaction Scheme 1
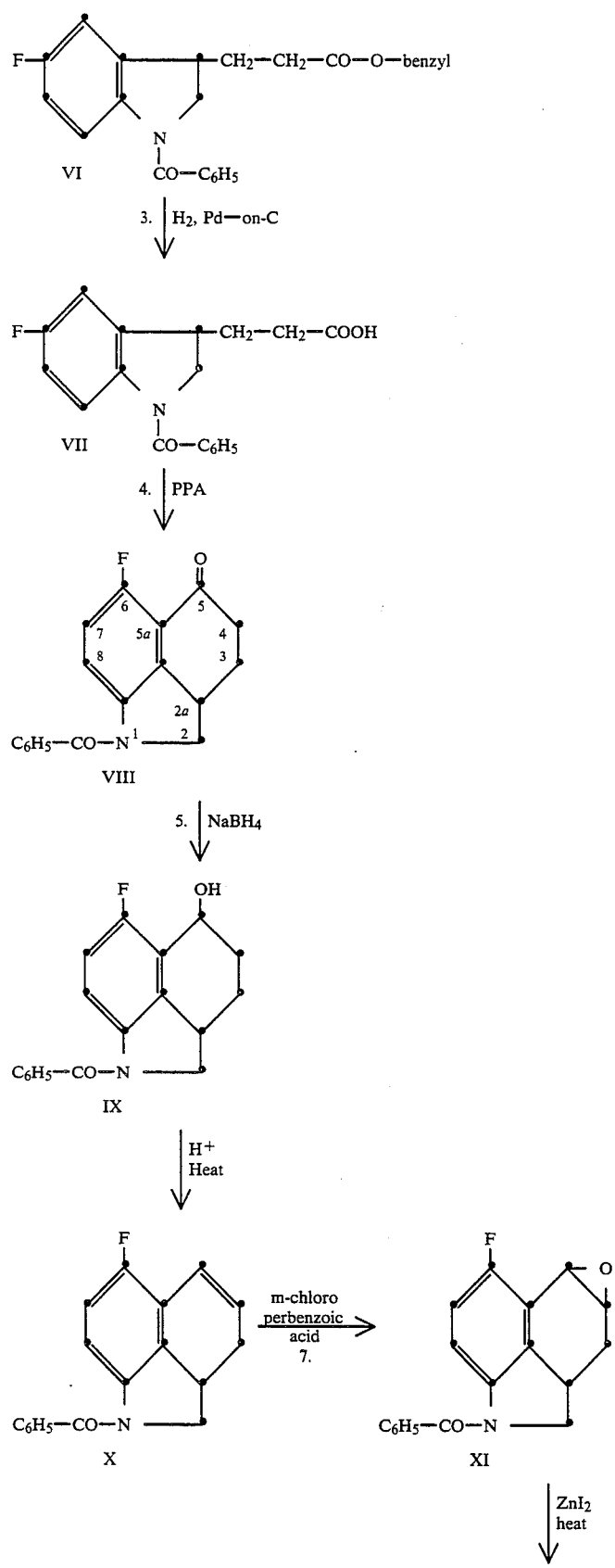

Reaction Scheme 1
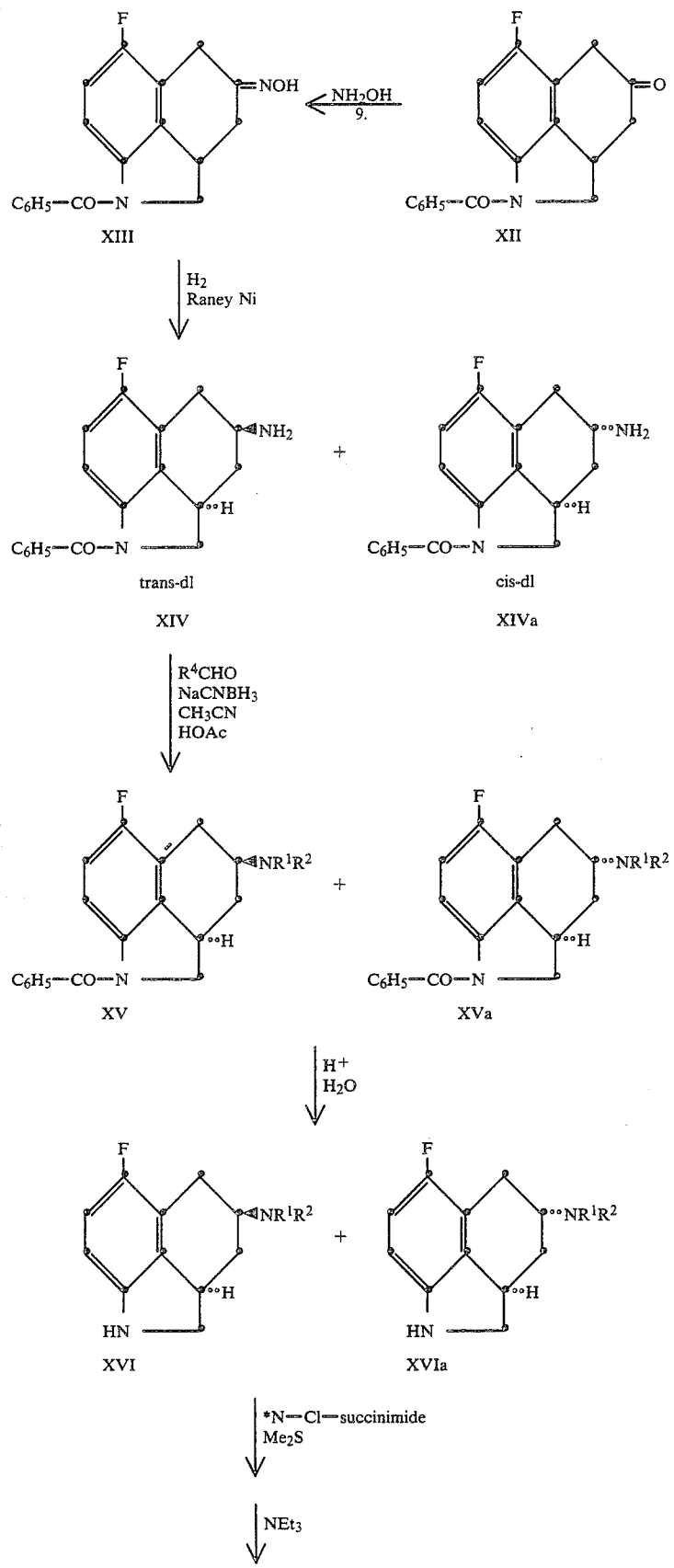

Reaction Scheme 1 -continued

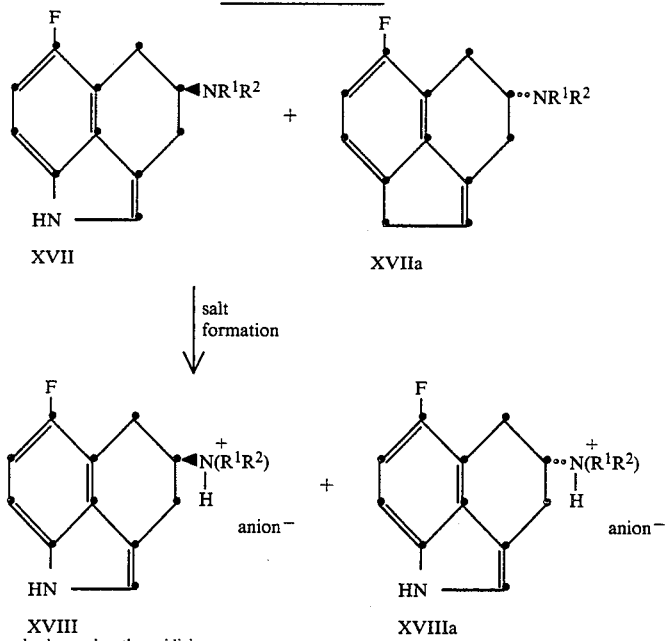

*MNO$_2$ can also be used as the oxidizing agent.

wherein R$^4$ is H, CH$_3$ or C$_2$H$_5$, and R$^1$ and R$^2$ have their previous meanings.

According to Reaction Scheme 1, wherein R$^4$ is ethyl and R$^1$ and R$^2$ are n-propyl for the sake of convenience, a benzyl 3-(5-fluoro-3-indolyl)propionate or the like ester (V) is reduced with (1) sodium cyanoborohydride to the corresponding 2,3-dihydro compound. Note: The Arabic numerals in parentheses refer to reagents used in Reaction Scheme 1. With the saturation of the 2,3 double bond, the 1-amino group becomes sufficiently basic to enable it to be protected with a standard amine protecting group such as an acyl function; i.e., as the benzoic acid amide. This protective group is formed by reacting the 2,3-dihydro compound with (2) an acyl halide or anhydride; for example, benzoyl chloride in the presence of pyridine, yields VI. The free acid (VII) is then prepared from the benzyl ester (VI) by hydrogenation (3) over a noble metal catalyst in an inert solvent. The noble metal catalyst of choice is palladium-on-carbon. The free acid thus produced—3-(5-fluoro-1-benzoyl-2,3-dihydro-3-indolyl)propionic acid—is cyclized (4) with a dehydrating agent, preferably polyphosphoric acid (PPA). This material is a particularly convenient cyclizing agent since it can also serve as a solvent for the cyclization reaction. Alternatively, the acid chloride can be prepared and cyclized in the presence of a Lewis acid, preferably AlCl$_3$—see Kornfeld et al., J.A.C.S., 78, 3087 (1956)—to yield the desired benz[c,d]indole. The cyclized product (VIII) is 1-benzoyl-5-oxo-6-fluoro-1,2,2a,3,4,5-hexahydrobenz[c,d]indole.

Reduction (5) of the oxo group with sodium borohydride in a lower alkanol such as ethanol yields the corresponding 5-hydroxy derivative (IX). This hydroxy derivative can be dehydrated (6) by heating in the presence of an acidic catalyst (p-toluene sulfonic acid for example) in an inert solvent to yield 1-benzoyl-6-fluoro-1,2,2a,3-tetrahydrobenz[c,d]indole (X). I prefer, however, to use an acidic ion exchange resin as the acid catalyst. The 4,5 double bond is then epoxidized (7) with a reagent such as m-chloroperbenzoic acid in an inert solvent to yield a 4,5-epoxy derivative (XI). Rearrangement of the epoxide (8) by heating in the presence of zinc iodide yields an isomeric ketone, (isomeric with VIII) 1-benzoyl-4-oxo-6-fluoro-1,2,2a,3,4,5-hexahydrobenz[c,d]indole (XII).

Next, the hydroxylamine derivative of this isomeric ketone (XIII) is formed (9) and the resulting oxime reduced with Raney nickel (10) to yield a mixture of amino derivatives, trans-dl and cis-dl-1-benzoyl-4-amino-6-fluoro-1,2,2a,3,4,5-hexahydrobenz[c,d]indole (XIV and XIVa). Alkylation (11) of the primary amine group by standard procedures, for example reductive alkylation with an aldehyde, R$^4$CHO, and sodium cyanoborohydride in acetonitrile, to which an equivalent of glacial acetic acid is added, yields the symmetrical dialkylamine; (XV and XVa). Treatment of the mixture of these cis-dl and trans-dl tertiary amines with aqueous acid (12) yields a mixture comprising trans-dl-4-dialkylamino-6-fluoro-1,2,2a,3,4,5-hexahydrobenz[c,d]indole and the corresponding cis-dl compound. Oxidation of this mixure with, for example, N-chloro succinimide (13) in the presence of dimethyl sulfide and triethylamine (14), yields ($\pm$)-4-dialkylamino-6-fluoro-1,3,4,5-tetrahydrobenz[c,d]indole (XVII and XVIIa represent the two enantiomers). The racemic mixture can readily be converted to the salt form (XVIII and XVIIIa) by standard procedures (15).

I have developed an alternate process for preparing ($\pm$)-4-dialkylamino-6-substituted-1,2,2a,3,4,5-hexahydrobenz[c,d]indole where the 6-substituent is Cl, Br or NO$_2$. This improved process is set forth in Reaction Scheme 2 below, using the case wherein the 6-substituent is Br.

Reaction Scheme 2

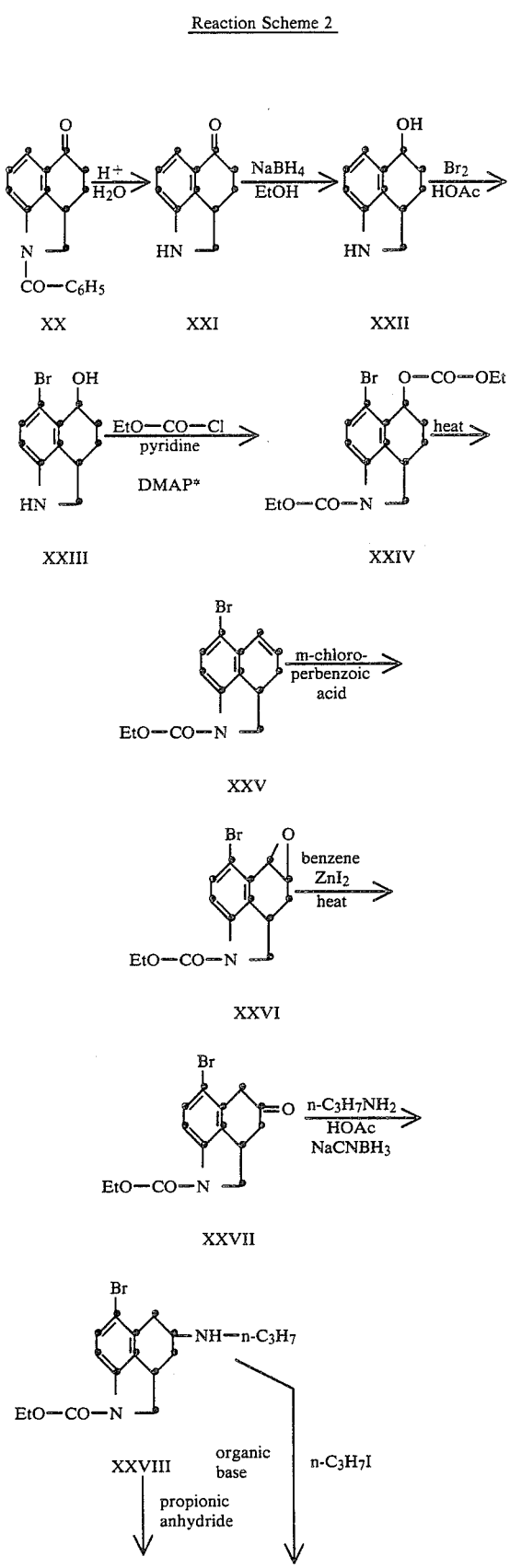

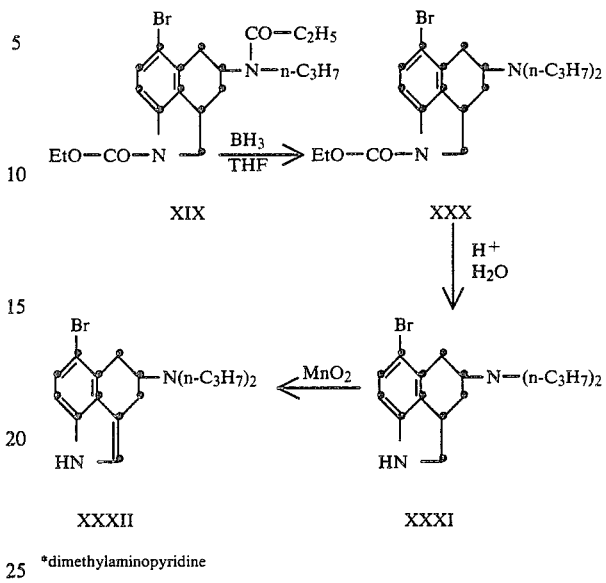

*dimethylaminopyridine

In the above reaction scheme, 1-benzoyl-5-oxo 1,2,2a,3,4,5-hexahydrobenz[c,d]indole (XX) [from Kornfeld et al, J.A.C.S., 78, 3887 (1956) compound 4] is hydrolysed in acid to 5-oxo-1,2,2a,3,4,5-hexahydrobenz[c,d]indole (XXI) (compound 10 of Kornfeld et al when R is H). The 5-ketone is reduced to a 5-hydroxyl[(±)-5-hydroxy-1,2,2a,3,4,5-hexahydrobenz[c,d]indole (XXII)] with an alkali metal borohydride or aluminumhydride in a mutual inert solvent. Bromination in acetic acid yields the (±)-6-bromo-5-hydroxy derivative (XXIII). This compound is then reacted with 2 moles of ethyl chloroformate to yield a (±)-1-ethoxycarbonyl-5-ethoxycarbonyloxy-6-bromo-1,2,2a,3,4,5-hexahydrobenz[c,d]indole (XXIV). This double acylation is conveniently carried out in pyridine solution (though other inert solvents may be used) containing an organic base catalyst such as DMAP. Heating the 5-ethoxy carbonyloxy compound results in dehydration to produce 1-ethoxycarbonyl-6-bromo-1,2,2a,3-tetrahydrobenz[c,d]indole (XXV). Epoxidation of the double bond using, conveniently, m-chloroperbenzoic acid or other peracid as in Reaction Scheme 1 with the corresponding 1-benzoyl derivative (X→XI). Rearrangement of the epoxide on heating with $ZnI_2$ yields the 4-oxo derivative (XXVII). Here again, the reaction conditions from Reaction Scheme 1 (XI→XII) can be employed. Reductive amination with n-propylamine and $NaCNBH_3$ yields (±)-1-ethoxycarbonyl-4-n-propylamino-6-bromo-1,2,2a,3,4,5-hexahydrobenz[c,d]indole (XVIII). This secondary amine can then be alkylated with propionic anhydride and the N-propionyl group reduced with $BH_3$ or $NaCNBH_3$ in TFA to yield the 4-di-n-propyl compound, (±)-1-ethoxycarbonyl-4-di-n-propylamino 6-bromo-1,2,2a,3,4,5-hexahydrobenz[c,d]indole (XXXI). Alternatively, the secondary amine XXVIII can be alkylated as with n-propyliodide in the presence of an organic base to yield XXXI directly. Finally, hydrolysis of the 1-ethoxycarbonyl amide yields XXXI, oxidation of which with $MnO_2$ or with N-chlorosuccinimide in the presence of dimethyl sulfide yields a 2,2a-didehydro derivative (XXXII). In general, the reaction conditions from Reaction Scheme 1 are operative here. (XVI+XVIa to XVII+XVIIa). The ultimate product of this reaction (XXXII) is the desired intermediate (±)-4-di-n-propylamino-6-bromo-1,3,4,5-tetrahydrobenz[c,d]indole.

Reaction of the thus-formed 6-bromo derivative with cuprous cyanide or an alkali or alkaline earth cyanide and cuprous iodide in 1-methyl-2-pyrrolidone solution yields the 6-cyano derivative, hydrolysis of which with base (KOH, NaOH) in a lower alkanol yields (±)-4-di-n-propylamino-6-carboxamido-1,3,4,5-tetrahydrobenz[c,d]indole. Replacement of the 6-bromo with CN is preferably carried out on the indole (XXXII) rather than on the indoline (XXXI).

The above reaction sequence has been illustrated with respect to the preparation of a 4-di-n-propyl derivative. It will be apparent to those skilled in the art that substitution of methyl, ethyl or allyl amine for n-propylamine in the preparation of XXVIII would yield a 4-methyl, ethyl or allyl amino group. Likewise the thus formed secondary amine could be acylated (XXVIII where the amine group is n-propyl but could be Me, Et or allyl) with formic, acetic, acrylic or propionic acid and the N-acyl group reduced to an alkyl or allyl group to form a compound of the formula

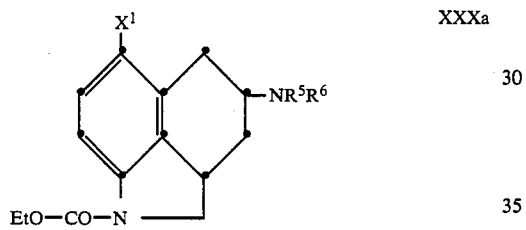

XXXa wherein $X^1$ is $NO_2$ or Br, and $R^5$ and $R^6$ are individually methyl, ethyl, n-propyl or allyl. It will be noted that the above procedure provides an easy route to unsymmetrically substituted C-4 tertiary amines.

Alternatively, the secondary amine (XXVIII where the amine group is n-propyl (but could be methyl, ethyl or allyl) can be directly alkylated with $CH_3I$, $C_2H_5I$, n-propyl iodide or allyl bromide to yield the same tertiary amine (XXXa).

The 6-chloro derivatives can be prepared in a fashion similar to the preparation of the 6-bromo derivative but chlorine is more resistant to replacement with a cyano radical, and the chloro compound is thus not as useful as an intermediate.

Alternatively, a 1-benzoyl-4-dialkylamino-1,2,2a,3,4,5-hexahydrobenz[c,d]indole can be nitrated to yield, after removal of the benzoyl protecting group and oxidation of the hexahydroindoline to a tetrahydroindole, compounds according to IV in which S is $NO_2$. This 6-nitro derivative is a particularly useful intermediate in that the nitro group can be reduced to a 6-amino function and thus produces compounds according to IV above in which X is $NH_2$.

When the 4-amine function ($R^1R^2N$) is other than di-n-propyl and X is CN, a different synthetic route is preferably employed to prepare compounds of formula IV. This alternate route also prepares compounds of formula IV where both $R^1$ and $R^2$ are n-propyl. This alternate route is shown in the following reaction scheme.

Reaction Scheme 3

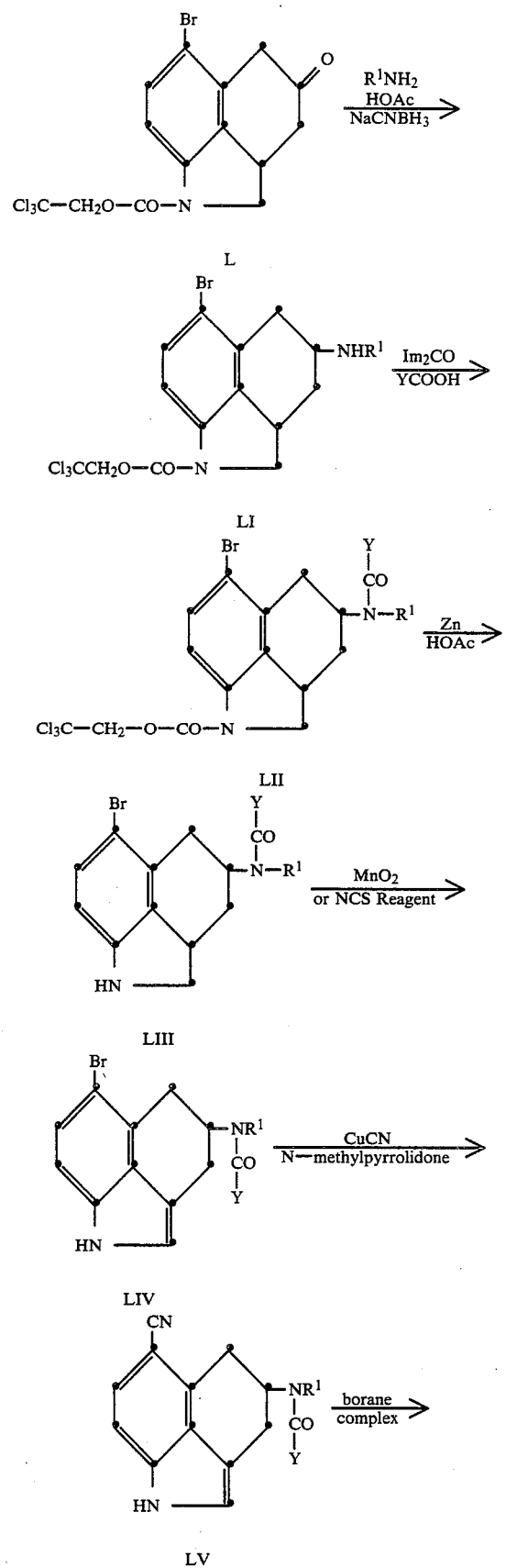

-continued
Reaction Scheme 3

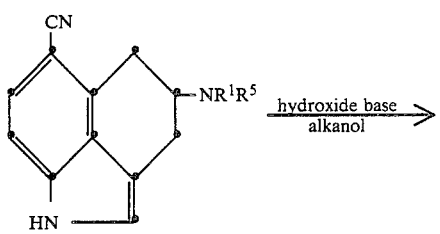

LVI

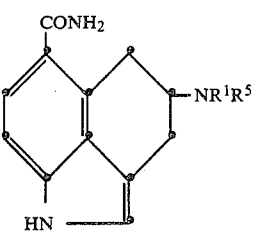

LVII

In Reaction Scheme 3, $R^1$ is hydrogen, methyl, ethyl or n-propyl; $R^5$ is methyl, ethyl or n-propyl;

Y is hydrogen, methyl, ethyl, or chloromethyl (this latter group is hydrolyzed from LV-LVI);

$Im_2CO$ is bis-imidazole carbonyl.

Compound LIV when $R^1$ is hydrogen is selectively hydrolyzed to remove the Y—CO moiety (e.g. basic hydrolysis such as MeOH, KOH). The product has a primary amine at C-4. The primary amine can then be reductively alkylated with an aldehyde $R^{10}CHO$ where $R^{10}$ is H, methyl, ethyl or vinyl to yield compounds of formula IV where $R^1$ and $R^2$ are $R^5$ and $R^6$, and X is Cl, Br or CN.

The CN groups (LVI) can then be hydrated with base, i.e. KOH in a $C_1$–$C_4$ alkanol to yield the carboxamide (LVII).

Reducing agents useful in converting LV to LVI are borane complex reagents such as $BH_3$-$(CH_3)_2S$, $BH_3$-pyridine, $BH_3$-$N(CH_3)_2$, $BH_3$-THF, or $B_2H_6$ in an inert solvent, such as THF.

In Reaction Scheme 3, the step from formula L to LI utilizes similar chemistry to that in Reaction Scheme 1 (XXVII to XXVIII), except that, in Reaction Scheme 3, acetic acid and $NH_3$ can be used to produce a 4-moiety of $NH_2$. The 4-amino group is converted to the benzyloxycarbonyl derivative by conventional methods. The $Cl_3C$-$CH_2$-$O$-$CO$ moiety is used as a 1-position protecting group since it is readily removed by reductive cleavage with Zn and acetic acid, which reaction does not affect the C-4 carbamate function present (LII).

The C-4 amine function (LI) is acylated with formic, acetic, a cyclic or propionic acid using $Im_2CO$, bisimidazolcarbonyl, to aid the acylation. Other condensing agents which can be employed include N,N'-disubstituted carbodiimide, and bis-imidazolyl sulfone.

As previously stated, the reductive cleavage of the N-1 protecting group (LII) does not affect the C-4 amide. Other N-1 protecting groups which are subject to reductive cleavage can also be used.

The LIII to LIV oxidation step is the same as XXXI and XXXII in Reaction Scheme I.

Alternatively, the 6-CN derivative (LV) is hydrolyzed to the 4-$NHR^5$-6-carboxylic acid derivative, then alkylated with $R^1$ halide to yield the 4-$R^1R^5$-6-carboxylic acid derivative. The 6-carboxylic acid moiety is coupled with $NH_3$ and a peptide coupling agent (e.g. $Im_2CO$, DCC and others) to provide the compounds of formula IV where X is $CONH_2$ and $R^1$ and $R^2$ are individually methyl, ethyl, n-propyl or allyl, provided that only one of $R^1$ or $R^2$ is allyl.

Similarly, the 6-CN-4-($NR^5$-COY) derivative (LV) is reduced to provide the 6-CN-4-($NR^5R^1$) derivative, which then has the 6-CN hydrolyzed to 6-COOH. The reaction then proceeds as described in the previous paragraph to yield the same 6-$CONH_2$ product of formula IV.

Compounds according to IV above have a single asymmetric center at C-4 and occur commonly as a racemate. However, compounds according to VIII through XVI and XVIa have an additional asymmetric center at C-2a, which center is removed by the oxidative procedures. Thus, compounds IX, XIV, XIVa, XV, XVa, XVI and XVIa each have two asymmetric centers (at C-2a and C-4) and exist as two racemic pairs conveniently designated as the trans-dl and the cis-dl racemates.

Compounds of formula IV wherein X is $NO_2$ or $NH_2$ are prepared according to the following reaction scheme.

Reaction Scheme 4

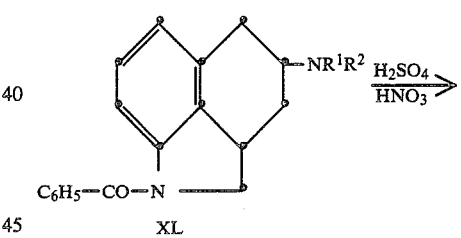

XL

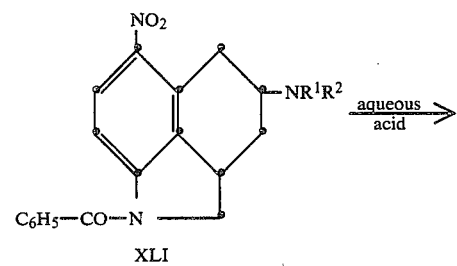

XLI

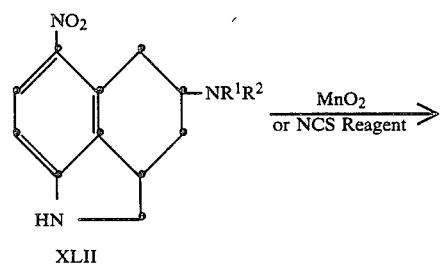

XLII

-continued
Reaction Scheme 4

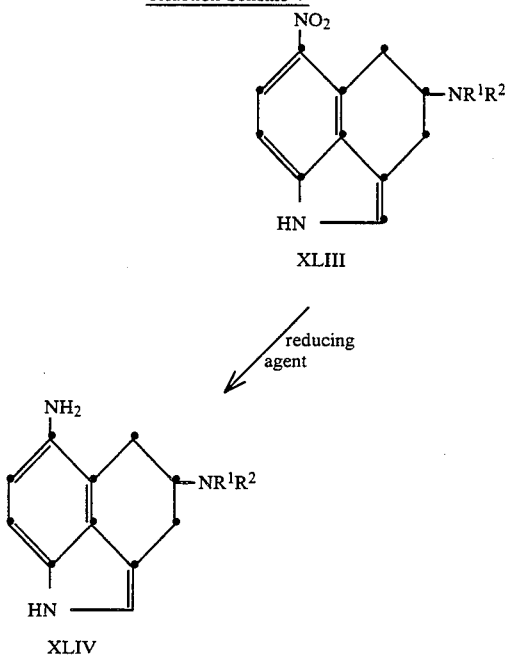

In Reaction Scheme 4, $R^1$ and $R^2$ are defined as before.

In Reaction Scheme 4, for example, a 1-benzoyl-4-dialkylamino-1,2,2a,3,4,5-hexahydrobenz[c,d]indole can be nitrated to yield, after removal of the benzoyl protecting group and oxidation of the indoline to a indole, compounds according to IV in which X is $NO_2$. This 6-nitro derivative is a particularly useful intermediate in that the nitro group can be reduced to a 6-amino function and thus produces compounds according to IV above in which X is $NH_2$.

This invention is further illustrated by the following specific examples.

EXAMPLE 1

Preparation of (±)-4-Di-n-propylamino-6-bromo-1,2,2a,3,4,5-hexahydrobenz[c,d]indole A mixture containing 5.0 g. of 5-oxo-1,2,2a,3,4,5-hexahydrobenz[c,d]indole in 100 ml. of ethanol was treated with 1.63 g. of sodium borohydride in portions. The resulting mixture was stirred for about four hours after which time the bulk of the ethanol was removed in vacuo. The resulting residue was taken up in water, and the aqueous mixture acidified with 3M hydrochloric acid. The aqueous solution was filtered, and the filtrate treated with dilute aqueous sodium hydroxide. (±)-5-Hydroxy-1,2,2a,3,4,5-benz[c,d]indole formed in the above reaction was insoluble in the basic medium and precipitated. The precipitate was collected, washed with water and then dried. Four and seventy-two hundredths grams of (±)-5-hydroxy-1,2,2a,3,4,5-hexahydrobenz[c,d]indole (93% yield) were obtained. The material was one spot by TLC; m.p.=205° C.

Analysis Calculated: C, 75.83; H, 6.94; N, 8.04. Found: C, 75.75; H, 7.16; N, 7.89.

A solution of 35 g. of (±)-5-hydroxy-1,2,2a,3,4,5-hexahydrobenz[c,d]indole in 900 ml. of cold glacial acetic acid was treated with 22 g. of bromine dissolved in 100 ml. of glacial acetic acid. After the bromine color had been discharged, the acetic acid was removed in vacuo. The residue, comprising a mixture of (±)-5-hydroxy-6-bromo-1,2,2a,3,4,5-hexahydrobenz[c,d]indole and the corresponding 6,8-dibromo derivative was diluted with water and the aqueous mixture made basic with 5M aqueous sodium hydroxide. The hexahydrobenz[c,d]indoles, being insoluble in base, precipitated, and the precipitate was collected. Recrystallization of the precipitate from methanol yielded about 3 g. of the dibromo derivative plus about 12.5 g. of the monobromo derivative and a considerable quantity of a crystal fraction which was a 1:1 mixture of starting material and monobromo derivative. (±)-5-Hydroxy-6-bromo-1,2,2a,3,4,5-hexahydrobenz[c,d]indole thus formed melted at about 172° C. with decomposition. Twenty-four and one tenth grams (47% yield) of the 6-bromo derivative were obtained by recrystallization of various fractions. The product as obtained still contained a small amount of the dibromo impurity.

A reaction mixture was prepared by dissolving 27.43 g. of (±)-5-hydroxy-6-bromo-1,2,2a,3,4,5-hexahydrobenz[c,d]indole in 100 ml. of pyridine and then adding in dropwise fashion 25 ml. of ethyl chloroformate over a 20 minute period. About 0.5 g. of 4-(N,N-dimethylamino)pyridine (DMAP) were added, and the resulting reaction mixture stirred at room temperature for about four hours. The reaction mixture was then quenched by pouring into 1 liter of an ice-water mixture. An oil which separated crystallized almost immediately. The crystals were collected and washed thoroughly with water. The dried ester amide was a faintly pink solid melting above 215° C. with decomposition; yield=40.48 g. (94%). Analysis indicated that some 6,8-dibromo compound continued as a contaminate.

Forty and one tenth grams of (±)-1-ethoxycarbonyl-5-ethoxycarbonyloxy-6-bromo-1,2,2a,3,4,5-hexahydrobenz[c,d]indole were pyrolized in four different ten gram runs at 215°-220° C. under a nitrogen atmosphere. Each run required 25-30 minutes of heating. The four dark oily residues were combined, and the combined residues taken up in toluene. The toluene solution was chromatographed over silica. One and four tenths grams of starting material were recovered from fractions containing it but the main product—1-ethoxycarbonyl-6-bromo-1,2,2a,3-tetrahydrobenz[c,d]indole—was recrystallized from a hexane/toluene solvent mixture containing predominantly hexane to yield 19.36 g. including a second crop, from hexane alone. Yield=65% corrected for recovered starting material. The compound melted at 122°-123° C.

Analysis Calculated: C, 54.56; H, 4.58; N, 4.55; Br, 25.93. Found: C, 54.59; H, 4.61; N, 4.41; Br, 25.84.

The unsaturated product from the above step was epoxidized as follows:

A solution of 7.5 g. of 1-ethoxycarbonyl-6-bromo-1,2,2a,3-tetrahydrobenz[c,d]indole in 250 ml. of chloroform was cooled to about 0° C. with an ice/salt mixture. Six grams of 85% of m-chloroperbenzoic acid were added. The reaction mixture was stirred at about 0° C. for one hour and was then kept at refrigerator temperature overnight. The reaction mixture was washed successively with 1N aqueous sodium hydroxide, saturated aqueous sodium bisulfite, again with 1N aqueous sodium hydroxide and finally with brine. The organic solution was dried, and the solvent removed in vacuo. The resulting solid residue was recrystallized from a toluene/hexane solvent mixture. The first crop material obtained weighed 7.33 g. and melted at 126°-8° C.; total yield (2 crops)=98%.

Analysis Calculated: C, 51.87; H, 4.35; N, 4.32; Br, 24.65. Found: C, 51.83; H, 11.33; N, 4.16; Br, 24.31.

A solution of 7.5 g. of 1-ethoxycarbonyl-4,5-epoxy-6-bromo-1,2,2a,3,4,5-hexahydrobenz[c,d]indole obtained as above in 50 ml. of benzene was added slowly to a refluxing solution of 1 g. of zinc iodide in 450 ml. of benzene which had been dried by distilling off 50 ml. of the benzene-water azeotrope. Reflux under a nitrogen atmosphere was continued for one hour after the addition had been completed. The reaction mixture was cooled. The supernate was decanted, and the decanted solution washed with water and then with brine. The solution was dried and the solvent removed therefrom in vacuo. The residue, comprising 1-ethoxycarbonyl-4-oxo-6-bromo-1,2,2a,3,4,5-hexahydrobenz[c,d]indole formed in the above reaction was crystallized from a toluene/hexane solvent mixture. Five and thirty-six hundredths grams (71% yield) of crystalline product melting at 186°-8° C. were obtained.

Analysis Calculated: C, 51.87; H, 4.35; N, 4.32; Br, 24.65. Found: C, 51.75; H, 4.29; N, 4.50; Br, 24.80.

A reaction mixture was prepared from 14 g. of 1-ethoxycarbonyl-4-oxo-6-bromo-1,2,2a,3,4,5-hexahydrobenz[c,d]indole, 28.3 g. of n-propylamine, 4.9 ml. of glacial acetic acid and 300 ml. of acetonitrile. The reaction mixture was stirred under a nitrogen atmosphere for about one hour. 3 Å molecular sieves were added to absorb water. Next, 5.6 g. of sodium cyanoborohydride were added followed by 14 ml. of glacial acetic acid. This new reaction mixture was stirred for an additional two hours at which time 7 ml. of glacial acetic acid were added. The reaction mixture was stirred for another two hours, and another 7 ml. of glacial acetic acid added. Finally, the supernate was decanted from the molecular sieves, and the bulk of the volatile constituents were removed in vacuo. The residual solution was poured into cold 2N aqueous sodium hydroxide. The alkaline mixture was extracted with methylene dichloride. The methylene dichloride extract was washed with 0.5N aqueous sodium hydroxide and then with brine. The solvent was removed in vacuo. The resulting residue was dissolved in 1N aqueous hydrochloric acid to which methanol had been added. This acidic solution was washed with ether, and the ether wash discarded. The acidic solution was then made basic with 5N aqueous sodium hydroxide, and the now insoluble (±)-1-ethoxycarbonyl-4-n-propylamino-6-bromo-1,2,2a,3,4,5-hexahydrobenz[c,d]indole formed in the above reaction separated and was extracted into methylene dichloride. The methylene dichloride extract was separated, and the solvent removed therefrom to yield 16.7 g. of an orange oil which was used in the next step without further purification.

The above crude product was dissolved in 50 ml. of acetonitrile, 3 ml. of n-propyl iodide and 2 ml. of diisopropylethylamine. This solution was allowed to remain in the dark for about three weeks. At this point in time, the solvent was removed under reduced pressure, and the residual mixture partitioned between ether and 0.5N aqueous sodium hydroxide. The organic layer was separated, and the aqueous alkaline layer extracted several times more with ether. The ether extracts were combined and the combined extracts washed with brine and then dried. The ether was removed in vacuo to yield a residue. Xylene was added to the residue and removed by evaporation to remove any remaining diisopropylethylamine. The unpurified residue slowly crystallized. The crystals were dissolved in 20 ml. of methylene dichloride and 1 ml. of acetic anhydride was added thereto. After about an hour, the volatile constituents were removed in vacuo and the resulting residue dissolved in methylene dichloride. The methylene dichloride solution was stirred with aqueous saturated sodium carbonate to remove any excess acetic anhydride. The methylene dichloride layer was separated, and the methylene dichloride removed by evaporation. The residue was dissolved in a mixture of dilute hydrochloric acid and methanol. The resulting cloudy solution was washed with ether and the ether was discarded. The acidic layer was then made basic with 5N aqueous sodium hydroxide and the now insoluble base which separated was extracted into methylene dichloride. Evaporation of the solvent gave a moist crystalline residue. The residue was treated with hexane, and the hexane solution separated from hexane-insoluble brown oil by decantation. The hexane was evaporated in vacuo, and the residue chromatographed over 25 g. of silica gel using ethyl acetate as the eluant. Fractions containing the desired material were combined and the solvent removed therefrom in vacuo. The white, crystalline residue was transferred to a filter paper using cold isooctane. A total yield of 2.39 g. of (±)-1-ethoxycarbonyl-4-di-n-propylamino-6-bromo-1,2,2a,3,4,5-hexahydrobenz[c,d]indole was obtained in two crops. m.p.=90°-94° C.

Analysis Calculated: C, 58.68; H, 7.14; N, 6.84; Br, 19.52. Found: C, 58.98; H, 6.88; N, 6.59; Br, 19.74.

Alternatively, a solution of 15.7 g. of the crude secondary amine. (±)-1-ethoxycarbonyl-4-n-propylamino-6-bromo-1,2,2a,3,4,5-hexahydrobenz[c,d]indole in 80 ml. of pyridine was cooled to about 0° C. Sixteen ml. of propionic anhydride were added slowly. The solution was allowed to remain at ambient temperature overnight. The bulk of the pyridine solvent was removed under vacuum, and the residual solution was stirred with an excess of aqueous sodium carbonate for several hours to remove any unreacted propionic anhydride and any by-product propionic acid. The aqueous mixture was extracted with methylene dichloride, and the methylene dichloride extract separated and washed with 0.5M aqueous sodium hydroxide, 1N hydrochloric acid and brine. The organic solution was dried and the solvent removed therefrom in vacuo leaving a viscous oil. The oil was dissolved in 50 ml. of THF and this solution added over about a 15 minute period to 85 ml. of 1M diborane in THF kept at about 0° C. After the addition had been completed, the cooling bath was removed, and the reaction mixture heated to reflux temperature for about 1.5 hours. The reaction mixture was then cooled to about 0° C. and 50 ml. of methanol were added cautiously. The resulting reaction was stirred overnight at room temperature. The methanol was removed in vacuo. Additional methanol was added and again removed by evaporation. The resulting residue began to solidify. The semisolid residue was partitioned between diethyl ether and 1M hydrochloric acid containing added methanol. The solid which precipitated as a result of these operations was collected by filtration. The filtrate was made basic by the addition of aqueous sodium hydroxide, and the alkaline mixture extracted with methylene dichloride. The above ether layer, the methylene dichloride extract and the separated solid were combined and the solvent evaporated. The residue was heated with wet DMSO, and this solution was then diluted with water plus sufficient 1M aqueous sodium hydroxide to maintain basic conditions.

The alkaline mixture was extracted with ether. The ether extract was in turn extracted with 1M hydrochloric acid containing some methanol. The acidic extract was again made basic, and the resulting alkaline mixture extracted with methylene dichloride. The methylene dichloride extracts were combined. Upon evaporation of the solvent, fifteen and fifty-nine hundredths grams of crude salmon colored compound were obtained. The solid was dissolved in ethyl acetate and chromatographed over silica gel. Fractions containing the desired material were combined and the solvent removed therefrom in vacuo. Recrystallization of the resulting solid from isooctane gave (±)-1-ethoxycarbonyl-4-di-n-propylamino-6-bromo-1,2,2a,3,4,5-hexahydrobenz[c,d]indole melting 87°–9° C.; yield=14.8 g. (94%).

A solution of 1 g. of the above tertiary amine in 10 ml. of 6N hydrochloric acid was heated to reflux temperature under nitrogen overnight. TLC indicated that only a trace of starting material remained and that the chief product was (±)-4-di-n-propylamine-6-bromo-1,2,2a,3,4,5-hexahydrobenz[c,d]indole. The acidic solution was poured into dilute aqueous sodium hydroxide, and the resulting alkaline layer extracted with methylene dichloride. The methylene dichloride extract was separated and the separated extract washed with brine and then dried. Evaporation of the solvent yielded a viscous oil which crystallized upon cooling. Recrystallization of the precipitate from isooctane gave 0.683 g. (83% yield) of (±)-4-di-n-propylamino-6-bromo-1,2,2a,3,4,5-hexahydrobenz[c,d]indole melting at about 62°–3° C.

Analysis Calculated: C, 60.53; H, 7.47; N, 8.31; Br, 23.69. Found: C, 60.71; H, 7.57; N, 8.30; Br, 23.78.

A run on a larger scale (14.8 g. of starting material) gave an 88% yield of the desired hydrolysis product.

EXAMPLE 2

Preparation of (±)-4-Di-n-propylamino-6-nitro-1,2,2a,3,4,5-hexahydrobenz[c,d]indole One-half gram of (±)-1-benzoyl-4-di-n-propylamino-1,2,2a,3,4,5-hexahydrobenz[c,d]indole from U.S. Pat. No. 4,110,339, column 3, line 49, in 5 ml. of 18M sulfuric acid was prepared in the cold and the resulting solution kept at ice bath temperature. Seven hundredths ml. of 90% nitric acid were added thereto in dropwise fashion via a pipette. The solution was stirred in the cold for about one hour and then poured over ice. The acidic mixture was neutralized by the careful addition of solid sodium carbonate. (±)-1-Benzoyl-4-di-n-propylamino-6-nitro-1,2,2a,3,4,5-hexahydrobenz[c,d]indole formed in the above reaction, being insoluble in the alkaline layer, separated and was extracted into methylene dichloride. The methylene dichloride layer was separated, washed with water and then dried. The solvent was removed in vacuo, and the crude residue chromatographed over Florisil using toluene containing increasing amounts (2–5%) of ethyl acetate as the eluant. Fractions shown by TLC to contain the desired material were combined and the solvent evaporated therefrom to yield a viscous red oil weighing 0.35 g. (61% yield). The red oil was used without further purification since the nmr was in agreement with the proposed structure.

The above material was dissolved in 7 ml. of 6N hydrochloric acid, and the resulting solution heated to reflux temperature under a nitrogen atmosphere for about two hours. At this point, TLC indicated no more starting material remained. The reaction was quenched with cold 5N aqueous sodium hydroxide. The free base was extracted with methylene dichloride. The methylene dichloride extract was washed with brine and then dried. TLC indicated only one mobile spot. The solvent was removed, and the residue chromatographed over Florisil using ethyl acetate as the eluant. Fractions containing the desired product were collected, the solvent removed therefrom and the residue crystallized from isooctane. (±)-4-Di-n-propylamino-6-nitro-1,2,2a,3,4,5-hexahydrobenz[c,d]indole thus prepared melted at 97°–100° C.; weight=0.194 g. (69% yield).

Analysis Calculated: C, 67.30; H, 8.31; N, 13.85. Found: C, 67.47; H, 8.21; N, 13.71.

EXAMPLE 3

Preparation of N-formyl (±)-4-methylamino-6-cyano-1,3,4,5-tetrahydrobenz[c,d]indole A solution of 16.8 g. of (±)-5-oxo-1,2,2a,3,4,5-hexahydrobenz[c,d]indole in 100 ml. of pyridine was stirred at ice bath temperature while 16 ml. of 2,2,2-trichloroethylchloroformate was added slowly over a 10 minute period. The reaction mixture was allowed to warm to room temperature under an $N_2$ atmosphere at which temperature it was stirred for an additional 3 hours. A majority of the pyridine was removed in vacuo. The resulting residue was partitioned between toluene and water. The toluene layer was separated and the aqueous layer extracted twice more with equal volumes of toluene. The toluene extracts were combined and the combined extracts washed several times with 1N hydrochloric acid (until the separated aqueous layer was acid to litmus). The combined toluene extracts were evaporated in vacuo. The resulting residue was recrystallized from toluene/hexane (1:1) to give 31.62 g. (93% yield of (±)-(2,2,2-trichloroethoxycarbonyl-5-oxo-1,2,2a,3,4,5-hexahydrobenz[c,d]indole melting at about 130°–132° C.

Following the procedure of Example 1, 31.0 g of (±)-1-(2,2,2-trichloroethoxycarbonyl)-5-oxo-1,2,2a,3,4,5-hexahydrobenz[c,d]indole were reduced with $NaBH_4$ in ethanol to yield (±)-1-(2,2,2-trichloroethoxycarbonyl)-5-hydroxy-1,2,2a,3,4,5-hexahydrobenz[c,d]indole; yield=30.1 (97%); m.p.=119°–121° C. (from ethanol).

A solution was prepared by dissolving 23.41 g of (±)-1-(2,2,2-trichlorethoxycarbonyl)-5-hydroxy-1,2,2a,3,4,5-hexahydrobenz[c,d]indole in 190 ml. of chilled (0° C.) trifluoroacetic acid (TFA). When solution was complete, 9.58 g. of dibromocyanuric acid were added in small amounts (1.25 hr. addition time). The reaction mixture was stirred for 2 hours at about 0° C. TLC in 100% methylene chloride indicated that no starting material remained. The reaction mixture was chilled and then made basic (to litmus) by the addition of an excess of 5N aqueous sodium hydroxide. The alkaline mixture was extracted with two 200 ml. portions of $CH_2Cl_2$. The combined $CH_2Cl_2$ extracts were washed with dilute aqueous sodium hydroxide. Two grams of tetrabutylammonium hydrogen sulfate were added to the dilute sodium hydroxide and the $CH_2Cl_2$ layers shaken with the NaOH solution until TLC indicated that all bi-product 5-trifluoroacetate had been hydrolyzed back to the 5-hydroxy derivative. The $CH_2Cl_2$ was removed in vacuo and the residue chromatographed over silica gel using $CH_2Cl_2$ as the eluant. Fractions containing the desired 6-bromo derivative were combined and the solvent removed. Recrystallization of the residue from diethylether provided (±)-1-(2,2,2-trichloroethoxycarbonyl)-5-hydroxy-6-bromo- 1,2,2a,3,4,5-benz[c,d]indole and melted at about 123°–125° C.; yield (2 crops)=18.74 g (65%).

Analysis Calculated: C, 39.15; H, 3.05; N, 3.26; Br, 18.60. Found: C, 39.34; H, 3.85; N, 3.44; Br, 18.38.

Mass spectrum: M+ =429

A reaction mixture was prepared by placing 18.74 g. of the above 6-bromo derivative, 475 ml. of toluene, 8 g. of Amberlyst®15, an ion exchange resin known to catalyze dehydration, in a 1 l. round-bottom flask equipped with magnetic stirrer, Dean-Stark trap, reflux condenser and drying tube. The reaction mixture was heated to reflux. After one hour, TLC revealed no remaining starting material. The solution was decanted from the Amberlyst® beads, and then decolorized with carbon. The decolorizing solution was filtered through hyflo supercel. The filtrate was evaporated to dryness in vacuo. $CH_2Cl_2$ was added and the solvent again removed in vacuo. The residue was crystallized from hexane. Yellowish crystals of (±)-1-(2,2,2-trichlorethoxycarbonyl)-6-bromo-1,2,2a,3,-tetrahydrobenz[c,d]indole, thus prepared melted at about 95°–99° C. Recrystallization from ether gave crystals melting at 98°–101° C. (96% yield).

Following the procedure of Example 1, the above $\Delta^{4,5}$ compound was epoxidized with m-chloroperbenzoic acid in $CHCl_3$ to yield (±)-1-(2,2,2-trichlorethoxycarbonyl)-4,5-epoxy-6-bromo-1,2,2a,3,4,5-hexahydrobenz[c,d]indole. 11.8 g. of epoxide was removed based on 17.64 g. of starting olefin. The epoxide was rearranged to the corresponding 4-oxo derivative by the procedure of Example 1 (zinc iodide in benzene), 7.29 g. (from 11.8 g. of starting olefin) of (±)-1-(2,2,2-trichlorethoxycarbonyl)-4-oxo-6-bromo-1,2,2a,3,4,5-hexahydrobenz[c,d]indole were obtained (62% yield).

A cold solution of 4.4 g. of methylamine in 100 ml. of acetonitrile was prepared. 1.9 ml. of acetic acid were added followed by 1.5 g. of sodium cyanoborohydride followed by about 5 g. of (±)-1-(2,2,2-trichlorethoxycarbonyl)-4-oxo-6-bromo-1,2,2a,3,4,5-hexahydrobenz[c,d]indole. The reaction mixture was continuously stirred and every two hours additional acetic acid was added in the following amounts—6.2 ml, 1.3 ml, and 1 ml., respectively. The reaction mixture was poured into ice-cold 2N aqueous NaOH. The alkaline mixture was extracted with $CH_2Cl_2$. The organic layer was separated and the solvent removed therefrom in vacuo. The residue was partitioned between 1N hydrochloric acid and ether. The ether layer was discarded. The acidic aqueous layer was made basic with NaOH and the now alkaline layer extracted with $CH_2Cl_2$. The organic extract was washed with brine and dried. 6.2 g. of (±)-1-(2,2,2-trichloroethoxycarbonyl)-4-methylamino-6-bromo-1,2,2a,3,4,5-hexahydrobenz[c,-d]indole, formed in the above reaction were obtained as a viscous oil. The oil was dissolved in 2.5 ml. of THF and this solution added to a solution of 5 g. of bis-imidazole carbonyl and 1.5 g. of 98% formic acid in 100 ml. of THF which had been stirred for 1 hour at room temperature under a nitrogen atmosphere. The reaction mixture was stirred for 3 hours at room temperature, at which time the solvent was removed in vacuo. The residue was partitioned between ether and saturated aqueous sodium bicarbonate. After standing overnight, a small amount of $CH_2Cl_2$ was added to dissolve residual solid. The alkaline aqueous phase was separated and the separated phase extracted with ether/$CH_2Cl_2$. The combined organic phases were washed with 1N hydrochloric acid and then with brine. The combined phases were dried and the solvent removed in vacuo. 7.48 g. of N-formyl(±)-1-(2,2,2-trichlorethoxycarbonyl-4-methylamino-6-bromo-1,2,2a,3,4,5-hexahydrobenz[c,-d]indole formed in the above acylation was obtained as a glass. The glassy residue was dissolved in 220 ml. of glacial acetic acid and 25 ml. of water. 23.4 g. of zinc dust were added and the mixture stirred under $N_2$ for 2 hours at room temperature. The suspension was filtered to remove unreacted zinc dust. The bulk of the acetic acid was then removed in vacuo. The oily residue was taken up in $CH_2Cl_2$ and saturated aqueous sodium bicarbonate added with care. A colorless zinc salt separated. The mixture was filtered through hyflo supercel. The organic layer was separated and the alkaline aqueous layer extracted with $CH_2Cl_2$. The combined $CH_2Cl_2$ extracts were washed with brine and then dried. Evaporation of the volatile constituents gave a glassy residue. The residue was dissolved in ethyl acetate. Crystals appeared. The bulk of the ethyl acetate was removed by decantation and toluene added. The mixture was chilled. Crystalline N-formyl(±)-4-methylamino-6-bromo-1,2,2a,3,4,5-hexahydrobenz[c,d]indole thus prepared was collected by filtration; weight=2.15 g; m.p.=177°–179° C.

Analysis calculated: C, 52.90; H, 5.12; N, 9.49; Br, 27.07; Found: C, 52.65; H, 5.31; N, 9.23; Br, 27.20.

Evaporation of the filtrate to dryness yielded an oil which was purified by chromatography over silica gel using ethyl acetate as the eluant, yield 1.22 g. of the oil as the epimer of the above crystalline product;

Analysis calculated: C, 52.90; H, 5.12; N, 9.49; Br, 27.07; Found: C, 53.14; H, 5.25; N, 9.21; Br, 27.02.

Total yield of both epimers=78%.

Two grams of the crystalline epimer were dissolved in 100 ml. of $CH_2Cl_2$. Eight grams of activated $MnO_2$ were added and the resulting suspension sonicated at 50–55 KHz under $N_2$ for 3 hours. The reaction mixture was filtered and the solvent evaporated to dryness in vacuo, leaving as a residue 1.63 g. of N-formyl(±)-4-methylamino-6-bromo-1,3,4,5-tetrahydrobenz[c,d]indole. The oily epimer, 1.15 g, was similarly oxidized to yield 1.02 g. of N-formyl(±)-4-methylamino-6-bromo-1,3,4,5-tetrahydrobenz[c,d]indole. The two N-formyl products were combined, dissolved in hot ethyl acetate containing 5% methanol, and chromatographed over 50 g. of silica gel using ethyl acetate as eluant. The product from the column was recrystallized affording 2.17 g. (69%) of N-formyl(±)-4-methylamino-6-bromo-1,3,4,5-tetrahydrobenz[c,d]indole. m.p. 204°–205° C.

Analysis Calculated: C, 53.26; H, 4.47; N, 9.56; Br, 27.26; Found: C, 53.00; H, 4.67; N, 9.28; Br, 27.06.

A mixture of 0.70 g. of cuprous cyanide, 1.00 g. of N-formyl(±)-4-methylamino-6-bromo-1,3,4,5-tetrahydrobenz[c,d]indole, and 10 ml. of N-methyl-2-pyrolidone was heated at 200° C. under $N_2$ for 4 hours. After cooling, the mixture was poured into water and $CH_2Cl_2$. The mixture was filtered, the aqueous phase was washed with $CH_2Cl_2$. The organic phase and $CH_2Cl_2$ washings were combined, washed with 1N HCl, then with NaCl solution, and dried over $Na_2SO_4$. The solvent was removed in vacuo and the residue was chromatographed over silica gel using ethyl acetate as eluant. The fractions containing the desired product were combined and evaporated to yield 0.39 g. (48%) of N-formyl(±)-4-methylamino-6-cyano-1,3,4,5-tetrahydrobenz[c,d]indole. m.p. 205°–207° C.

Analysis calculated: C, 70.28; H, 5.48; N, 17.56; Found: C, 70.56; H, 5.51; N, 17.30.

EXAMPLE 4

Preparation of (±)-4-Di-n-propylamino-6-bromo-1,3,4,5-tetrahydrobenz[c,d]indole

A suspension of 0.44 g. of N-chlorosuccinimide in 16 ml. of toluene was chilled to about 0° C. Three tenths ml. of dimethylsulfide were added. After 15 minutes, the reaction mixture was cooled in a dry ice-acetone bath to about −60° C. Six tenths grams of (±)-4-di-n-propylamino-6-bromo-1,2,2a,3,4,5-hexahydrobenz[c,d]indole (prepared in Example A) and 2 ml. of toluene were added over a 15 minute period. The reaction mixture was stirred at about −60° C. for about two hours at which point 0.8 ml. of triethylamine were added. The cooling bath was removed and stirring continued for about 2½ hours at ambient temperature. The reaction mixture was then poured into cold 1N aqueous sodium hydroxide and the now alkaline mixture extracted several times with toluene. The toluene extracts were combined, and the combined extracts washed with brine and then dried. The solvent was removed and the resulting residue chromatographed over 15 g. of Florosil using a 1:9 ethyl acetate/toluene solvent mixture as the eluant. Fractions containing the desired product were combined and rechromatographed over silica using the same eluant. Fractions containing the desired product were again combined and the solvent evaporated therefrom to leave a slightly greenish oil. This oil was dissolved in about 20 ml. of pentane and filtered to remove a colorless precipitate. The pentane was then removed by evaporation in vacuo. A yellow green oil weighing 0.303 g. (51% yield) was obtained comprising (±)-4-di-n-propylamino-6-bromo-1,3,4,5-tetrahydrobenz[c,d]indole formed in the above oxidation. The product crystallized upon standing; m.p.=72°-3° C.

Analysis Calculated: C, 60.90; H, 6.91; N, 8.36; Br, 23.83; Found: C, 60.77; H, 6.87; N, 8.28; Br, 23.61.

Alternatively, a solution of 1 g. of (±)-4-di-n-propylamino-6-bromo-1,2,2a,3,4,5-hexahydrobenz[c,d]indole and 50 ml. of hexane was prepared. Four grams of activated manganese dioxide were added and the resulting suspension sonicated (50–55 KHz) under a nitrogen atmosphere for about one hour. TLC at this point indicated almost no starting material remaining. The reaction mixture was suction filtered, and the precipitate of magnese dioxide obtained was thoroughly washed with fresh hexane. The hexane was removed from the filtrate and the resulting residue chromatographed as before. Fractions containing the desired indole were combined and the solvent removed by evaporation. Recrystallization of the resulting residue from isooctane yielded 0.62 g. (62% yield) of (±)-4-di-n-propylamino-6-bromo-1,3,4,5-tetrahydrobenz[c,d]indole melting at 73°-4° C.

EXAMPLE 5

Preparation of (±)-4-Di-n-propylamino-6-cyano-1,3,4,5-tetrahydrobenz[c,d]indole

A solution was prepared by dissolving 0.7 g. of cuprous cyanide in 10 ml. of N-methyl-2-pyrrolidone (previously purged with nitrogen). One gram of (±)-4-di-n-propylamino-6-bromo-1,3,4,5-tetrahydrobenz[c,d]indole was added to the cuprous cyanide solution. The solution was heated under a nitrogen atmosphere at 200° C. for one hour. The reaction mixture was then cooled and the cooled mixture partitioned between ethyl acetate and dilute aqueous ammonium hydroxide. The alkaline layer was extracted several times with ethyl acetate. The ethyl acetate layers were combined and the combined layers washed successively with dilute aqueous ammonium hydroxide, dilute aqueous ethylenediamine and brine. The ethyl acetate layer was then dried and the solvent removed therefrom. The residual oil was dissolved in ether, and the ether solution washed twice with brine. The ether layer was separated and the ether removed therefrom in vacuo. The residue was next dissolved in ether, and the ether diluted with several volumes of petroleum ether. The supernate was decanted and the dark residual oil treated with a mixture of ether and petroleum ether again. The combined supernates were evaporated yielding a viscous orange oil as a residue. Chromatography of this residue over silica gel using 1:10 ethyl acetate/toluene as the eluant yielded fractions containing the desired (±)-4-di-n-propylamino-6-cyano-1,3,4,5-tetrahydrobenz[c,d]indole formed in the above reaction. Recrystallization of the solids thus obtained from a toluene/hexane solvent mixture yielded crystalline material melting at 132°-3° C.; yield=44%.

Analysis Calculated: C, 76.83; H, 8.24; N, 14.83; Found: C, 76.56; H, 8.09; N, 14.86.

EXAMPLE 6

Preparation of (±)-4-Di-n-propylamino-6-carbamoyl-1,3,4,5-tetrahydrobenz[c,d]indole About 1.5 g. of powdered potassium hydroxide were suspended in 10 ml. of distilled t-butanol and 0.3 ml. of DMSO. Three tenths grams of (±)-4-di-n-propylamino-6-cyano-1,3,4,5-tetrahydrobenz[c,d]indole were added. The mixture was heated to reflux temperature under a nitrogen atmosphere for about 72 hours. At this point, TLC indicated only partial reaction. Reflux was continued for another 24 hours. The reaction mixture was then quenched by the addition of cold water and the aqueous mixture extracted with methylene dichloride. The organic layer was separated and the separated layer washed with brine and then dried. Evaporation of the solvent yielded a residue which was chromatographed over Florisil using ethyl acetate containing increasing amounts of methanol, up to 10%. The starting material was eluted with 5% methanol/95% ethyl acetate, and the desired product, (±)-4-di-n-propylamino-6-carbamoyl-1,3,4,5-tetrahydrobenz[c,d]indole, was eluated with the 10% methanol/90% ethyl acetate. Fourteen hundredths grams of product were obtained and about 0.17 g. of starting material. The recovered starting material was treated as above with powdered KOH in t-butanol and DMSO. The second hydration mixture was heated to reflux temperature for about four days. The reaction mixture was quenched as before, but TLC indicated that hydration reaction was still not complete. However, the 6-carbamoyl derivative obtained from the second run was about 0.5 g. Again, the recovered starting material was treated as before and refluxed with base for about one week and an additional quantity of the 6-carbamoyl derivative obtained. All the fractions containing (±)-4-di-n-propylamino-6-carbamoyl-1,3,4,5-tetrahydrobenz[c,d]indole were combined and the combined fractions chromatographed over Florisil using ethyl acetate followed by 1:1 methanol/ethyl acetate as the eluant. The starting material was eluted with the ethyl acetate. The (±)-4-Di-n-propylamino-6-carbamoyl-1,3,4,5-tetrahydrobenz[c,d]indole, thus isolated, melted at 163°-5° C. after successive recrystallizations from toluene/hexane and toluene. One hundred seventy-three thousands grams of the compound was obtained (54% yield).

Analysis Calculated: C, 72.21; H, 8.42; N, 14.03; Found: C, 72.23; H, 8.27; N, 13.57.

EXAMPLE 7

Preparation of (±)-4-Di-n-propylamino-6-nitro-1,3,4,5-tetrahydrobenz[c,d]indole

A solution was prepared by dissolving 0.15 g. of (±)-4-di-n-propylamino-6-nitro-1,2,2a,3,4,5-hexahydrobenz[c,d]indole (prepared in Example B) in 10 ml. of methylene dichloride. Six tenths grams of manganese dioxide were added and the mixture sonicated at 50–55 KHz under a nitrogen atmosphere for about ten hours. The mixture was filtered through supercel and the supercel washed with fresh methylene dichloride. The solvent was removed from the filtrate, and the resulting residue was chromatographed over silica gel using toluene containing increasing amounts (5–10%) of ethyl acetate. Fractions containing (±)-4-di-n-propylamino-6-nitro-1,3,4,5-tetrahydrobenz[c,d]indole were combined to yield 0.102 g. of that product. Recrystallization from a toluene/hexane solvent mixture gave 0.087 g. (58% yield) of compound melting at 130°–2° C.

Analysis Calculated: C, 67.75; H, 7.69; N, 13.94. Found: C, 67.74; H, 7.74; N, 13.81.

EXAMPLE 8

Preparation of (±)-4-Dimethylamino-6-cyano-1,3,4,5-tetrahydrobenz[c,d]indole

A mixture of 0.42 g. of N-formyl(±)-4-methylamino-6-cyano-1,3,4,5-tetrahydrobenz[c,d]indole (prepared in Example 3) and 12 ml. of THF was treated with 1.9 ml. of 2M borane-methyl sulfide complex in THF. After stirring the mixture for 2 hours at room temperature, the reaction was quenched with 1 ml. of methanol, the solvents removed in vacuo, and the residue taken up in 2 ml. of DMSO. To the solution was added a few drops of saturated $NaHCO_3$ solution. The mixture as heated on a steam bath for 10 minutes, water added, and product extracted with $CH_2Cl_2$. The extracts were washed with NaCl solution, dried over $Na_2SO_4$, and the solvents removed in vacuo. The crystalline residue was chromatographed over Florisil using ethyl acetate as eluant. The fractions containing product were evaporated, and the residue crystallized from ethyl acetate/toluene to yield 0.24 g. (60%) of (±)-4-dimethylamino-6-cyano-1,3,4,5-tetrahydrobenz[c,d]indole. m.p. 196°–198° C. mass spectroscopy=225 (parent peak)

EXAMPLE 9

Preparation of (±)-4-Dimethylamino-6-carbamoyl-1,3,4,5-tetrahydrobenz[c,d]indole To a suspension of 1.25 g. of powered KOH in dry t-butanol was added 0.25 g. of 18-crown-6-ether followed by 0.20 g. of (±)-4-dimethylamino-6-cyano-1,3,4,5-tetrahydrobenz[c,d]indole. The mixture was refluxed for 48 hours under $N_2$, then 0.3 ml. of DMSO was added. The mixture was refluxed for another 72 hours. The mixture was then treated with 0.25 ml. of water then refluxed another 24 hours. The reaction was quenched with water and the product extracted with $CH_2Cl_2$. The extract was washed with brine, then dried over $Na_2SO_4$. The solvent was removed, and the residue was chromatographed over Florisil using 5% methanol/95% ethyl acetate followed by 10% methanol/90% ethyl acetate. (The former solvent gave starting material and the latter solvent gave the product.) The (±)-4-dimethylamino-6-carbamoyl-1,3,4,5-tetrahydrobenz[c,d]indole thus isolated weighed 2 mg (1%); $R_f$=0.10 (solvent system $CH_2Cl_2/CH_3OH$/concentrated $NH_4OH$, 45:5:1).

In the above procedures, use of ammonia in place of methylamine in the reaction with (±)-1-(2,2,2-trichloroethoxycarbonyl)-4-oxo-6-bromo-1,2,2a,3,4,5-hexahydrobenz[c,d]indole yields (±)-1-(2,2,2-trichlorethoxycarbonyl)-4-amino-6-bromo-1,2,2a,3,4,5-hexahydrobenz[c,d]indole. This primary amine can then be acylated with, for example, formic acid and bis-imidazolecarbonyl to yield an amide; which group is carried through the reductive (Zn and acetic acid) removal of the 1-(2,2,2-trichloroethoxycarbonyl) group to yield an indoline, oxidation with $MnO_2$ to yield an indole, replacement of the 6-bromo formation with cyanide to yield a 6-cyano group and finally hydrolysis (3N hydrochloric acid/THF) to yield (±)-4-amino-6-cyano-1,3,4,5-tetrahydrobenz[c,d]indole. The primary amine group can then be reductively alkylated with an aldehyde (formaldehyde, acetaldehyde, propionaldehyde) and, for example, sodium cyanoborohydride or other suitable borohydride reducing agent, to yield the dialkylamine function. The cyano group can then be hydrated to the carboxamide to yield a (±)-4-($C_1$-$C_3$ alkyl)amino-4-aminocarbonyl-1,3,4,5-tetrahydrobenz[c,d]indole.

The central serotonergic action of drugs according to IV above was demonstrated in two ways. The first method was to show inhibition of tritiated serotonin uptake according to the following protocol. (Weak inhibition of tritiated spiperone uptake was also determined.) Several (±)-4-di-n-propylamino-6-substituted-1,3,4,5-tetrahydroindoles plus the corresponding drug from Bach-Kornfeld U.S. Pat. No. 4,110,339 lacking a C-6 substituent were tested.

Brain tissue was obtained from 150–200 g. male Wistar rats. The cerebral cortex was dissected out and then homogenized and centrifuged according to the method described by Nelson and coworkers, *Mol. Pharmacol.*, 14, 983–995 (1978), using preincubation in buffer without added monoamine oxidase inhibitor in order to eliminate endogenous serotonin. For receptor binding, each sample contained 300–400 μg. of membrane protein and 10 μM pargyline in addition to the $^3$H-ligand in 1 ml. of 0.05M tris buffer, pH=7.4. The assay of serotinin binding was done following the method of Bennett and Snyder, *Mol. Pharmacol.*, 12, 373–389 (1976), and that for tritiated spiperone according to Peroutka and Snyder, *Mol. Pharmacol.*, 16, 687–699 (1979). The samples were incubated for 15 minutes at 37° and were then filtered through GF/C glass fiber filter pads using a Brandel M-24 cell harvester modified for receptor binding. After two 5 ml. rinses, the filter discs were put into scintillation vials and counted in 10 ml. of Amersham PCS scintillation fluid. Nonspecific binding of $^3$H-serotonin ($^3$H-5HT) was determined in the presence of $10^{-5}$M serotonin and of $^3$H-spiperone in the presence of $10^{-6}$M LSD. Specific binding was calculated as the difference between total binding with no added nonradioactive compound and the nonspecific binding. $IC_{50}$ values were determined where the $IC_{50}$ is the amount of substance causing 50 percent inhibition of the specific binding using 10–12 concentrations in the range of $10^{-9}$ to $10^{-4}$M. The concentrations of $^3$H-ligands were: serotonin (Amersham, 11 Ci/mmol), 2–3 nM; LSD (Amersham, 1.8 Ci/mmol), 1.8–2.6 nM; spiperone (Amersham, 20 Ci/mmol), 0.6–0.7 nM.

The results obtained, are set forth in Table 1.

TABLE 1
RECEPTOR BINDING

| Name of Compound | $^3$H-Ligand-IC$_{50}$* | |
|---|---|---|
|  | $^3$H-5HT | $^3$H-SPIP |
| (±)-4-di-n-propylamino-6-aminocarbonyl-1,3,4,5-tetrahydrobenz[c,d]indole | 60 | 4980 |
| (±)-4-di-n-propylamino-6-cyano-1,3,5,6-tetrahydrobenz[c,d]indole | 90 | 390 |
| (±)-4-di-n-propylamino-6-nitro-1,3,5,6-tetrahydrobenz[c,d]indole | 100 | 400 |
| (±)-4-dimethylamino-1,3,4,5-tetrahydrobenz[c,d]indole | 120 | 730 |

*Values are in nanomoles of inhibitor.

Secondly, as a measure of central serotonin agonist activity, the decrease of serotonin metabolites in brain was measured. Also the measure of dopamine agonist activity was indicated by changes in dopamine metabolites.

The following protocol was employed. 150-200 g. Wistar rats were given 0.3 mg./kg. subcutaneously of (±)-4-di-n-propylamino-6-substituted-1,3,4,5-tetrahydrobenz[c,d]indole. Then, 60 minutes later each rat was decapitated and the hypothalamus and striatum were dissected out and extracted. The amounts of homovanillic acid (HVA) and 3,4-dihydroxyphenylacetic acid (DOPAC) in the striatum and of 5-hydroxyindoleacetic acid (5HIAA) in the hypothalamus were measured by high-performance liquid chromatography, using electrochemical detection. Serum corticosteroids were also measured. Table 2 gives the results of this experiment. In the table, columns 1 and 2 give the substitution pattern in the compounds of formula IV, columns 3-5, the 5HT or dopamine metabolite concentrations, and column 6, the serum corticosteroids.

TABLE 2

| X | R$^1$ and R$^2$ | 5HIAA In Hypothalamus NMoles/G | Dopamine Metabolites In Striatum, NMoles/G | | Serum Corticosterone MCG/100 ML |
|---|---|---|---|---|---|
|  |  |  | DOPAC | HVA |  |
| CN | di-nPr | 2.34 ± .07 | 4.25 ± .25* | 2.27 ± .16* | 47 ± 4* |
| NO$_2$ | di-nPr | 2.29 ± .03* | 3.74 ± .11 | 2.02 ± .20* | 49 ± 2* |
| CONH$_2$ | di-nPr | 1.58 ± .03* | 6.23 ± .56 | 4.12 ± .27 | 49 ± 2* |
|  | (control) | 2.59 ± .11 | 5.58 ± .38 | 4.24 ± .27 | 7 ± 1 |

Compounds were injected at 0.3 mg./kg. s.c. 1 hour before rats were killed.
*statistically significant Drugs which have central serotonin agonist activity are useful as antidepressants. The compounds of formula IV which have such central serotonergic activity to a marked degree with minimal agonist or antagonist actions toward NE or dopamine should be particularly useful in that their use would not be accompanied by side effects common to presently marketed antidepressants, particularly the antimuscarinic effect. Several of the marketed antidepressants are also monamine oxidase inhibitors, a nonspecific amine oxidase linked with metabolic degradation of both catecholamines and serotonin, which activity is also lacking in the drugs of formula IV.

The novel drugs of formula IV can be administered parenterally as an isotonic solution of a pharmaceutically acceptable salt. Preferably, however, the drugs are administered orally. For such route of administration, the drug is mixed with one or more pharmaceutical excipients and loaded into empty telescoping gelatin capsules or compressed into tablets, each tablet or capsule to contain a unit antidepressant dosage of the drug.

I claim:

1. A 4-substitutedamino-6-substituted-1,3,4,5-tetrahydrobenz[c,d]indoles of the formula

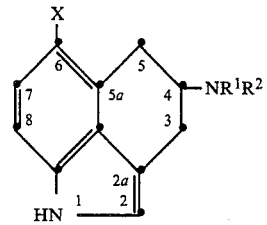

wherein R$^1$ and R$^2$ are individually hydrogen, methyl, ethyl, n-propyl or allyl; R$^1$ is additionally Y—CO where Y is H; CH$_3$; C$_2$H$_5$ or CH$_2$=CH; and X is a halogen, CN, CONH$_2$, NH$_2$ or NO$_2$, and pharmaceutically acceptable salts thereof.

2. A compound according to claim 1 in which X has its previous meaning and R$^1$ and R$^2$ are individually methyl, ethyl, n-propyl or allyl.

3. A compound according to claim 1 in which X is CONH$_2$.

4. A compound according to claim 1 in which X is cyano.

5. A compound according to claim 1 in which X is nitro.

6. A compound according to claim 1 in which X is Br, CN, CONH$_2$, NH$_2$ or NO$_2$.

7. A compound according to claim 2 in which X is (CO)NH$_2$.

8. A compound according to claim 1 in which X is Br.

9. A compound according to claim 2 in which R$^1$ and R$^2$ are the same.

10. A compound according to claim 9 in which R$^1$ and R$^2$ are both n-propyl.

11. A compound according to claim 9 in which R$^1$ and R$^2$ are both methyl.

12. A compound according to claim 2, said compound being (±)-4-di-n-propylamino-6-nitro-1,3,4,5-tetrahydrobenz[c,d]indole.

13. The hydrochloride salt of a compound according to claim 7.

14. A compound according to claim 1, said compound being (±)-4-(di-n-propyl)amino-6-aminocarbonyl-1,3,4,5-tetrahydrobenz[c,d]indole.

15. A compound according to claim 1 in which R$^2$ has its previous meaning, R$^1$ is Y—CO wherein Y is methyl, ethyl or vinyl; and X is CN, or Br.

16. A pharmaceutical formulation in unit dosage form comprising per unit dosage, an amount of a compound according to claim 2 to alleviate the symptoms of depression plus one or more pharmaceutical excipients.

17. A formulation according to claim 16 in which (±)-4-di-n-propylamino-6-aminocarbonyl-1,3,4,5-tetrahydrobenz[c,d]indole is the active drug.

18. A method of treating depression which comprises administering to a depressed individual an antidepressant dose of a compound according to claim 2.

19. A therapeutic process according to claim 18 in which (±)-4-di-n-propylamino-6-aminocarbonyl-1,3,4,5-tetrahydrobenz[c,d]indole, optionally in the form of a pharmaceutically acceptable salt, is administered.

20. A formulation according to claim 17 in which the unit dosage formulation is adapted for oral administration.

21. A therapeutic process according to claim 18 in which the drug is administered by the oral route.

22. A formulation according to claim 16 in which (±)-4-dimethylamino-6-aminocarbonyl-1,2,4,5-tetrahydrobenz[cd]indole is the active drug.

23. A therapeutic process according to claim 18 in which (±)-4-dimethylamino-6-aminocarbonyl-1,3,4,5-tetrahydrobenz[cd]indole optionally in the form of a pharmaceutically acceptable salt, is administered.

* * * * *